(12) United States Patent
Ting et al.

(10) Patent No.: US 6,918,879 B2
(45) Date of Patent: Jul. 19, 2005

(54) METHOD AND DEVICE FOR MONITORING BLOOD PRESSURE

(75) Inventors: Choon Meng Ting, Singapore (SG); Ngak Hwee Chua, Singapore (SG)

(73) Assignee: Healthstats International Pte. Ltd., Singapore (SG)

( * ) Notice: Subject to any disclaimer, the term of this patent is extended or adjusted under 35 U.S.C. 154(b) by 0 days.

(21) Appl. No.: 10/191,887

(22) Filed: Jul. 9, 2002

(65) Prior Publication Data

US 2003/0004421 A1 Jan. 2, 2003

Related U.S. Application Data

(63) Continuation-in-part of application No. 09/694,847, filed on Oct. 20, 2000, now Pat. No. 6,443,906.

(51) Int. Cl.[7] ................................................. A61B 5/02
(52) U.S. Cl. ......................... 600/485; 600/500; 600/503
(58) Field of Search ................................. 600/485, 490, 600/500–507

(56) References Cited

U.S. PATENT DOCUMENTS

| | | | | |
|---|---|---|---|---|
| 4,307,727 A | | 12/1981 | Haynes ........................ 600/485 |
| 4,331,154 A | * | 5/1982 | Broadwater et al. ......... 600/490 |
| 5,183,051 A | * | 2/1993 | Kraidin et al. ............... 600/500 |
| 5,243,992 A | * | 9/1993 | Eckerle et al. ............... 600/503 |
| 5,261,412 A | | 11/1993 | Butterfield et al. |
| 5,309,916 A | * | 5/1994 | Hatschek ..................... 600/485 |
| 5,406,952 A | * | 4/1995 | Barnes et al. ................ 600/485 |
| 5,485,848 A | | 1/1996 | Jackson et al. .............. 600/485 |
| 5,509,423 A | * | 4/1996 | Bryars ......................... 600/503 |
| 5,533,511 A | * | 7/1996 | Kaspari et al. .............. 600/485 |
| 5,535,753 A | * | 7/1996 | Petrucelli et al. ........... 600/485 |
| 5,551,437 A | * | 9/1996 | Lotscher ...................... 600/485 |
| 5,568,814 A | | 10/1996 | Gallant et al. ............... 128/672 |
| 5,772,601 A | * | 6/1998 | Oka et al. .................... 600/495 |
| 6,017,313 A | * | 1/2000 | Bratteli et al. ............... 600/485 |
| 6,290,650 B1 | | 9/2001 | Butterfield et al. ......... 600/485 |

FOREIGN PATENT DOCUMENTS

| | | |
|---|---|---|
| EP | 0297224 | 1/1989 |
| EP | 0968681 | 1/2000 |
| EP | 1074216 | 2/2001 |
| JP | 5329117 | 12/1993 |

OTHER PUBLICATIONS

"Ambulatory" Webster's Revised Unabridged Dictionary, 1998, p. 2.*

* cited by examiner

Primary Examiner—Robert L. Nasser
Assistant Examiner—Patricia C. Mallari
(74) Attorney, Agent, or Firm—Ladas and Parry LLP

(57) ABSTRACT

A device for continuously monitoring a user's arterial blood pressure has a sensor adapted to continuously detect the blood pressure and to generate signals representative thereof by contact with an external surface of the user's body at a location adjacent an artery. The sensor is securely held in operable contact with the user's body at the location. A microprocessor interprets the signals generated by the sensor to determine the actual arterial blood pressure. The sensor includes a projecting portion for detecting and transmitting changes in blood pressure, wherein the projecting portion is adapted to effect at least partial occlusion of the artery at the location.

14 Claims, 15 Drawing Sheets

METHOD AND DEVICE FOR MONITORING BLOOD PRESSURE

This application is a CIP Ser. No. 09/694,847 Oct. 20, 2000 now U.S. Pat. No. 6,443,906.

FIELD OF THE INVENTION

The present invention relates to a method and device for monitoring blood pressure. In particular, such method and device is non-invasive to the human body and the device is preferably portable.

BACKGROUND AND PRIOR ART

Hypertension is a silent killer. According to the National Health Survey, 1998, about 27.3% of the Singapore population between the ages of 30–69 years are hypertensive. This translates to about 600,000 hypertensives based on the 2.2 million people in this age group, of whom about half have not been previously diagnosed. The prevalence of hypertension and its related complications are on the rise, with:

1. one new hospital admission for stroke every hour;
2. 25% of stroke patients are <45 years old;
3. one heart attack every 3 hours as recorded by the Acute Myocardial Infarction Register;
4. more and younger patients requiring renal dialysis.

Such facts are not unique to Singapore. Many developed countries have comparable, if not higher, statistics. In other words, hypertension is a global problem of epidemic proportions.

In Singapore alone, there is at least one person coming down with stroke every hour. The numbers are rising year after year. Moreover, death from stroke in Singapore accounts for more than 12% of all deaths since 1996.

Together with heart ailment, it accounts for more than 32% of all deaths since 1996, i.e. more than one-third of all mortalities in Singapore.

Further, every year there are about 27,000 to 30,000 pregnancies leading to successful deliveries. Of these, thousands of pregnant women suffer from a condition called pre-eclampsia. This is a condition whereby the mother suffers from a rise in blood pressure during pregnancy. The blood pressure can rise to dangerous levels without warning and it can lead to convulsion and brain damage to the mother, and sudden intra-uterine death of the baby. The morbidity and mortality of pre-eclampsia is directly related to the level and control of blood pressure of the patient.

The central event linking the 3 major ailments is blood pressure. In fact, in many instances of strokes and heart attacks, the usual and final pathway is a sudden and dangerous rise in blood pressure before catastrophe strikes.

Therefore, the detection and prevention of further rises or falls in the final pathway holds the key to the prevention and reduction of strokes, heart attacks and eclampsia.

Currently, patients who suffer from the above illnesses are monitored either as outpatients or in-patients in a hospital. The majority of these are outpatients. When one visits a doctor, be it monthly or fortnightly, the blood pressure reading is obtained by using a blood pressure cuff sphygmomanometer. They use occlusive methods, i.e. air is pumped into the cuff to occlude the artery and is slowly released to finally allow the blood to overcome the resistance and flow through. A flow turbulence is thus set up and picked up by the doctor listening to it. The blood pressure is then recorded. The self-monitoring devices that are available on the market generally all use occlusive methods, the difference being the turbulence are picked up by various methods, such as via a microphone. In other words, the number of readings is totally dependent on the number of times that the artery is being occluded, whether it is manual or pre-set electronically. The monitoring is therefore not continuous, in the sense of having beat-to-beat readings.

To make matters worse, whenever the doctor detects a normal or "good" blood pressure in his clinic, he usually makes 3 assumptions:

1. the patient's blood pressure from the last test must be "good";
2. his blood pressure until the next test will be "good"; therefore, he will not have a stroke, heart attack or convulsion as in the case of a pre-eclampsic woman.

Unfortunately, these assumptions are far from the truth as the above incidents have revealed. Casual blood pressure measurements taken in the doctor's office or by the patients themselves are not necessarily representative of a person's 24-hours blood pressure. Therefore, it would be advantageous to be able to catch the "final pathway" of sudden changes in blood pressure/pulse, by being able to monitor a person's blood pressure continuously and be able to sound the alarm at the right time to prevent a catastrophe.

One method of continuously monitoring blood pressure is suggested in U.S. Pat. No. 5,485,848. That patent purports to disclose a non-invasive and non-intrusive portable device for monitoring a user's arterial blood pressure. However, that device has the disadvantage that it needs to fix a nominal or base pressure by fixing the strap tension. The calibration is also user-specific. It assumes that base pressure can be maintained constant for the calibration to work. It is not practically possible to fix the base pressure of a moving wrist by the methods described. At most, it only keeps the strap circumference constant, instead of keeping the pressure constant. By fixing the circumference of the strap, pressure changes are even greater with movement and changes in position of the hand. Thus, the wrist position cannot change. In practice, it is difficult to keep the pressure constant as a slight change in wrist pressure and sensor position affects readings to an appreciable extent. Furthermore, the calibration involves extrapolation and interpolation of readings. Therefore, user conditions must remain uniform, since one has to show a linear relationship which may not exist if user conditions are otherwise. In accordance with the described formula for calculating blood pressure, the pressure sensed by the piezoelectric film transducer is dependent on the area of contact, distance from the artery and source of the signal. These are factors which cannot practically be fixed with the described device.

To provide continuity in monitoring, the blood pressure must be measured on a beat-to-beat basis, as in intra-arterial monitoring.

The time-keeping function of a watch should be integrated with the blood pressure data, as this will provide a meaningful interpretation of the trend or pattern of blood pressure seen or recorded over a period of time. The downloading of data over time may become important in an unfortunate event of the death of a wearer.

Similarly, in the collection of data by the sensor, the position of the sensor and the fixation of the sensor must be considered. In order to accurately collect data from every beat of the heart, the sensor compartment must be able to receive reliable data with the wrist in different positions. In the prior art, the data can only be reliably collected when the hand is held fixed at a certain position, i.e. with restrictions. The prior art may try to overcome the movement of the strap by increasing the strap pressure. Usually, this is not only impractical, but undesirable as the compression of veins will cause significant congestion in the hand distal to it in just a few minutes. This can lead to numbness and further medical complications.

The Median Nerve at the Carpal Tunnel would be compressed causing numbness of the finger in a few minutes. As a result, the hand or fingers will swell, causing further congestion. This not only greatly affects the signal, but is harmful to the wearer. Therefore, the challenge is to be able to design the strap system that is comfortable to the wearer over a long period and holds the sensor in position well so as to allow for natural movement of the hand/wrist and collects the data accurately.

The donning and doffing of the wrist monitor and the whole calibration has to be simple and user-friendly for it to be of value for a person who is not medically trained.

However, there is overwhelming evidence in the past 3–4 years that demand us to take a new look at blood pressure monitoring. According to Professor Eoin O'Brien from the Beaumont Hospital, Dublin, Ireland, different individuals fall into distinctly different blood pressure patterns, which can only be identified by 24-hours tracings of the blood pressure (as opposed to single, momentary clinic/office reading). The 9 (not exhaustive) main blood pressure patterns identified are:

1. Normal Blood Pressure;
2. Borderline Hypertension;
3. Isolated Systolic Hypertension;
4. Isolated Diastolic Hypertension;
5. Systolic & Diastolic Hypertension with night time dip;
6. Systolic & Diastolic Hypertension without night time dip;
7. Nocturnal Hypertension;
8. White Coat Hypertension;
9. White Coat Normotension.

Naturally, each individual pattern has its own risks and implications that require its unique management, which may or may not require pharmacological intervention. Without 24-hours blood pressure tracings, White Coat Hypertensive patients may unwittingly be put at increased risk due to unnecessary treatment. On the other hand, certain blood pressure patterns may predispose an individual to increased risk of a stroke or heart attack and early recognition of these patterns allow appropriate treatment to be given to arrest or slow the progression of the disease.

Against this medical background and clinical deficiency, the object of the present invention is to provide an improved device and method for continuous and non-invasive monitoring of arterial blood pressure.

SUMMARY OF THE INVENTION

According to one aspect the present invention consists of a device for non-invasive continuous monitoring of a user's arterial blood pressure that is capable of being used as an ambulatory beat-to-beat blood pressure monitor (ABMP) including, sensor means adapted to continuously detect said blood pressure and to generate signals representative thereof by contact with an external surface of the user's body at a location adjacent an artery;

microprocessing means for interpreting said signals generated by the sensor means to determine actual arterial blood pressure;

wherein the microprocessing means is programmed to record a complete and continuous arterial pulse waveform.

In a further aspect the present invention consists in a method for continuous monitoring of a user's arterial blood pressure including the steps of:

recording a complete and continuous arterial pulse pressure waveform, locating at least the dicrotic notch and the diastolic trough within said continuous arterial pulse waveform, and calculating at least one parameter using said waveform and said diastolic trough and dicrotic notch locations.

It will be convenient to hereinafter describe the invention in greater detail by reference to the accompanying drawings which illustrate one particularly preferred embodiment. The particularity of the drawings and the related description is not to be understood as superseding the generality of the broad identification of the invention.

BRIEF DESCRIPTION OF THE DRAWINGS

The drawings relate to one preferred embodiment of the invention.

DETAILED DESCRIPTION OF A PREFERRED EMBODIMENT OF THE INVENTION

According to the preferred embodiment of the present invention, there are several major components in the design of the device. They are the sensor system to measure the blood pressure, a housing for the sensor, the strap system to secure the sensor relative to an artery and electronic processing unit housed in the watch head for calibration and other interfacing purposes.

Measuring of Blood Pressure

The principle behind the design of the present invention is to mimic the intra-arterial measurement of blood pressure. This intra-arterial method of blood pressure measurement is at present invasive to the human body.

Figure 1:
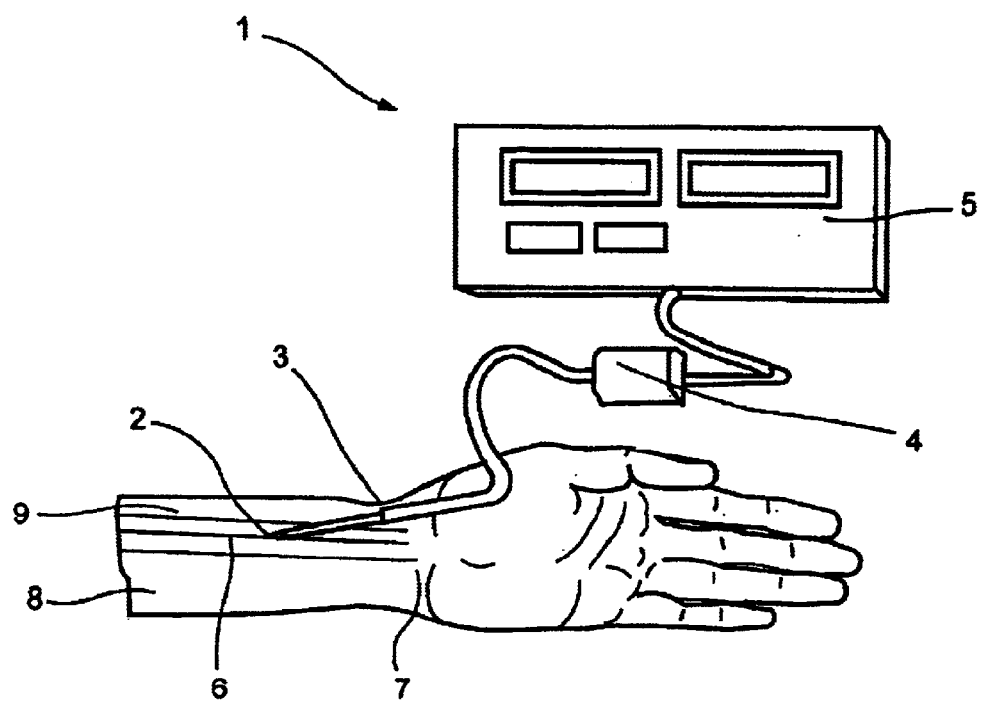
FIG. 1 is an illustration of an intra-arterial blood pressure monitoring device of the prior art.

FIG. 1 is an illustration of an intra-arterial blood pressure monitoring device 1 of the prior art. The intra-arterial blood pressure monitoring device 1 generally comprises an intra-arterial cannula 2, that is inserted into the radial artery 6 of a patient's wrist 7. As is apparent from FIG. 1, the radial artery 6 is adjacent to the radial bone 8. The intra-arterial cannula 2 is connected to a fluid interface 3, containing a fluid column. The fluid 5 interface 4 is connected by a tube to a microprocessor and sensor unit 4. The microprocessor and sensor unit 4 detects changes in the blood pressure in the radial artery 6 and this information is transmitted to a pressure display unit 5.

In the intra-arterial blood pressure measuring device 1 the blood pressure in the radial artery 6 is sensed, beat-to-beat by the blood column in the inducting cannula 2. This beat-to-beat change acts on the column of fluid, which is incompressible and will faithfully relay the pressure change to the microprocessor. The electronic change in signal is then converted to a digital form and displayed on a graph on the display 5, the systolic being the pressure value when the heart pumps, and diastolic, the pressure of the column at rest.

The primary disadvantage of the intra-arterial blood pressure monitoring device 1 is that it is invasive. The patient feels discomfort and pain as the intra-arterial cannula 2 is inserted into his skin 9 and artery 6. Furthermore, the device 1 is also not portable, such that it is normally only used in a hospital environment. It is not possible to monitor a person's blood pressure continuously when he is going about his normal daily activities. Intra-arterial measurements cannot be taken with any movement of the wrist. Therefore, the whole wrist must be immobilised, as during an operation.

This present invention utilises the principle of Applanation Tonometry to capture the arterial pulse waveform, from which the blood pressure patterns and other medically relevant parameters are derived. Unlike currently available devices, this breakthrough method is neither occlusive nor invasive, and is capable of continuous, 24-hours beat-to-beat monitoring In the design of the present invention, the whole system including the strap, the sensor and the wrist head have to be considered together in order to appreciate the similarity in principle to the intra-arterial cannula 2.

Components of the Sensor System

Figure 2:
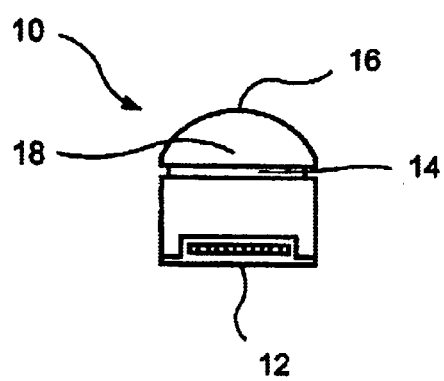
FIG. 2 is a side view of a sensor according to the preferred embodiment of the invention.
Figure 9:
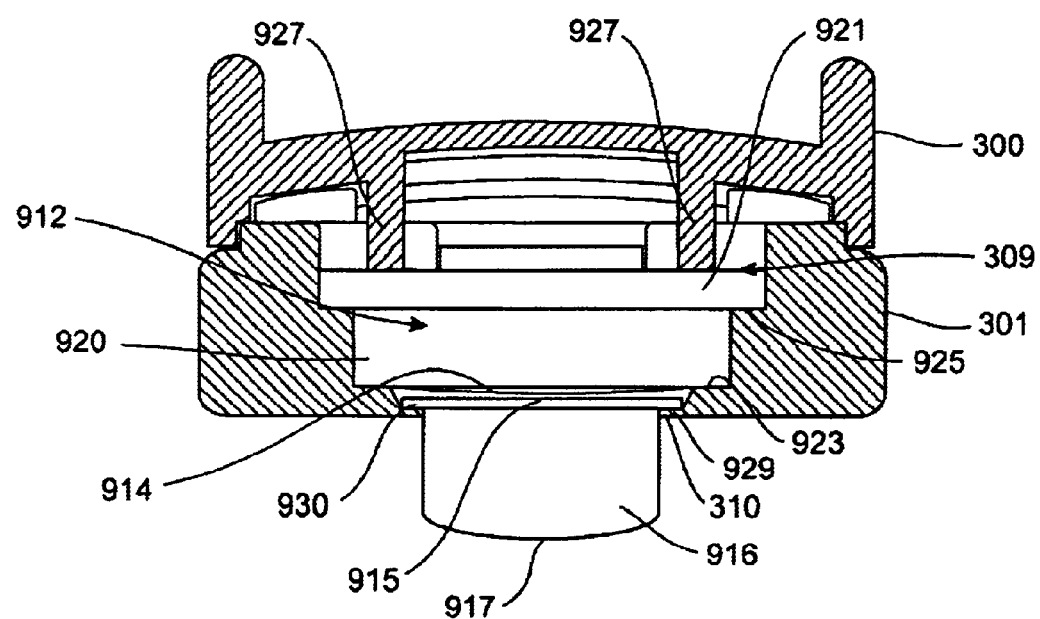
FIG. 9 is a cross sectional side elevation through the sensor and sensor housing according to the preferred embodiment of the invention illustrated in FIGS. 3A and 3B.

FIG. 2 is a side view of a sensor 10 according to one embodiment of the invention. An alternate variation of the sensor is shown in FIG. 9.

Referring to FIG. 2 the sensor 10 includes a transducer 12 which produces a voltage output according to pressure changes acting on its diaphragm 14. A plunger 16 is affixed next to the diaphragm 14 of the transducer 12.

The plunger 16 has a dome shaped or hemispherical head. The plunger 16 sits on the diaphragm 14 of the transducer 12. The purpose of the diaphragm 14 is to give a constant resting force on the transducer 12. The plunger 16 is able to float freely in a vertical direction due to a pre-determined gap between the base of plunger 16 and the diaphragm 14. The plunger 16 has an effective length which is the depth of the applanation, corresponding to a preferred range of 3 mm to 10 mm. The diameter of the plunger 16 is preferably between 3 mm to 8 mm which correspond to the physiological diameter of an artery.

In use the plunger 16 pushes into the wrist and partially occludes the radial artery. The hemispherical shape of plunger 16 ensures comfort over long hours of wearing and also enables pulsation to be faithfully transmitted to the transducer 12. Advantageously, it enables the transmission of the pulsation of the radial artery 20 to be picked up even though the wearer's hand may be at various positions as depicted in FIGS. 4 and 5.

A layer of gel 18 sits between the diaphragm 14 and the plunger 16, the gel layer 18 filters out interference and sharp changes due to unnatural movement. The gel layer 18 also dampens the noise to signal ratio.

Figure 3A:
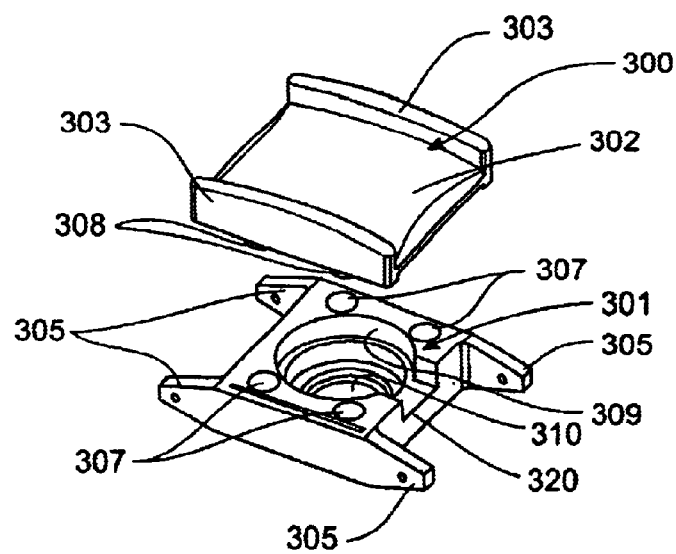
FIG. 3A is a top perspective view of a housing according to the preferred embodiment of the invention.
Figure 3B:
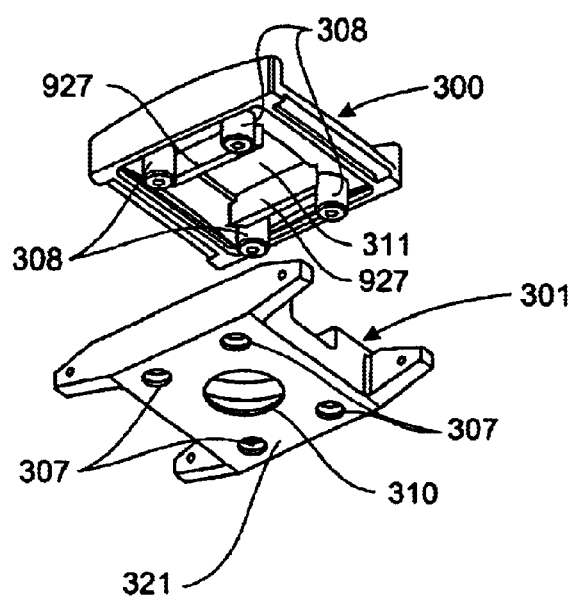
FIG. 3B is a bottom perspective view of a housing according to the preferred embodiment of the invention.
Figure 4:
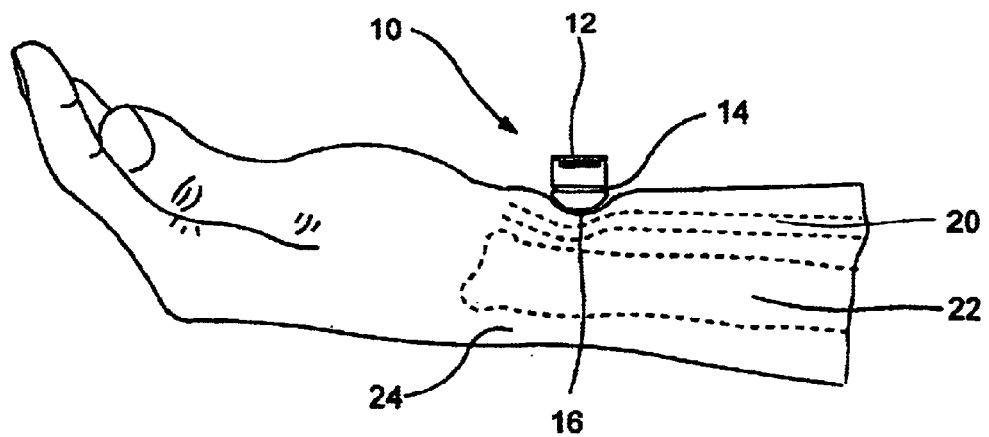
FIG. 4 is a side view of a sensor of FIG. 2 used on the wrist of a wearer and placed adjacent to and partially occluding the radial artery of the wearer.

Referring to FIG. 4, in that embodiment the sensor is fitted within a housing. The housing has an outer cover portion 300 and an inner carrier portion 301. The housing will be described further on with reference to FIGS. 3A and 3B. In this form the sensor includes a pressure transducer 912 which produces the voltage output according to pressure changes acting on its diaphragm 914. A plunger 916 has a domed head 917. The domed head 917 protrudes through a circular aperture 310 in the housing 301. It is free to move towards the pressure transducer 912. When not pressed toward the pressure transducer 912 there is a slight gap between the plunger 916 and the diaphragm 914 of pressure transducer 912. The pressure transducer is thereby free floating. This ensures there is no preload of the plunger 916 against the pressure transducer 912.

Figure 5:
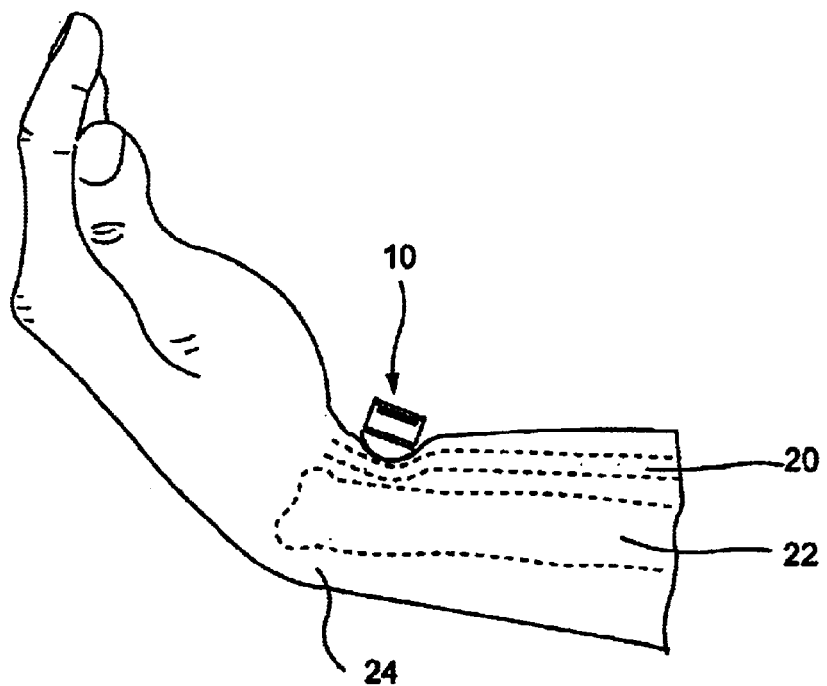
FIG. 5 is an illustration of the sensor placed next to the radial artery wherein the user's hand is flexed.

Referring to FIGS. 4 and 5 the plunger depth is selected so that in most normal wrists (e.g.: wrist 24), the plunger can occlude not more than half the diameter of the radial artery 20 when the strap is comfortably worn. This will enable full and faithful transmission of the arterial pulsation to be picked up, including the expansion of the arterial walls, the turbulence of the flow and the vibration transmitted along the artery wall from the heart.

The Sensor Housing

FIGS. 3A, 3B and 9 illustrate the preferred housing. The housing includes an outer cover portion 300 and an inner carrying portion 301. The outer cover portion 300 has a smooth convex outer surface 302 and a pair of side guards 303 the purpose of the convex outer surface and side guards will be set forth later with reference to the padding and anchoring system. The inward face of cover portion 300 includes a receptacle 311 for receiving the transducer 912. A set of protruding legs 308 extend from the inward face of cover portion 300 toward the carrying portion 301.

The carrying portion 301 includes a generally circular recess 309 for receiving the body of the transducer 912. The circular recess 309 includes a series of concentric terraces ending at a circular aperture 310. The circular aperture 310 opens between the recess 309 through the inward face 321 of the carrying portion 301. The pressure transducer 912 has a flattened cylindrical main body 920 and an flanged upper end 921. The main body 920 rests on second terrace 923 within the recess 309. The flange of the flanged upper end 921 rests on first terrace 925. A pair of locating members 927 extend downward from the cover portion 300. The locating members 927 press against the flanged upper end 921 of the transducer 912 and locate the transducer 912 against the terraces 923 and 925. The plunger 916 has an annular retaining flange 930 at its end distal from its domed end 917. The retaining flange 930 seats on third terrace 929. Third terrace 929 appears as a lip surrounding aperture 310. This lip retains the plunger 916 to the housing. The spacing between terraces 929 and 923, the plunger 916 and the diaphragm 914 of pressure transducer 912 are all such that when the plunger 916 is urged toward leaving the housing through aperture 310, but retained by terrace 929, a narrow space or gap 915 lies between the plunger 916 and the diaphragm 914. As referred to earlier this gap ensures there is no preload on the transducer 912.

The carrying portion 301 includes locating holes 307 in its outer surface, which receive the legs 308 of the cover portion 300. The carrying portion includes a notch 320 in the wall of recess 309. The notch 320 provides an opening to recess 309 with the cover portion 300 located on the carrying portion 301. This opening permits wiring connections to the sensor 10.

The carrying portion 301 includes a pair of connection legs 305 extending from either end. Each pair of connection legs 305 are adapted to receive and retain a spring loaded watch strap retaining bar.

FIG. 4 is a side view of the sensor 10 of FIG. 2 used on the wrist 24 of a wearer and placed adjacent to and partially occluding the radial artery 20 of the wearer. FIG. 5 is an illustration of the sensor 10 placed next to the radial artery wherein the user's hand is flexed.

Referring to FIGS. 4 and 5 the sensor 10 is preferably placed adjacent to the radial artery 20. The radial artery 20 at the wrist 24 has been chosen because firstly, it rests on the radial bone 22 dorsally. The radial bone 22 allows for full transmission of the pulsation to be felt as it is rigid and would not allow for any significant soft tissue compensation. Vertically, the sensor system 10 is locked in together with the watch straps and watch head as one immovable and unstretchable unit. The plunger 16 is thus behaving similarly to the intra-arterial cannula 2, and the fluid column 3. As the plunger 16 and the diaphragm 14 are the only moving units at each pulsation, the arterial pressure is accurately picked up as a waveform as each heart beat reaches the radial artery. Nevertheless, the advantage is that there is no need for the system to be invasive and it is portable.

The following reasons improve the functionality of the sensor system:
1. For a change in pressure between 0 mmHg–300 mmHg, the displacement of the diaphragm against the pressure variation forms a linear relationship. The range of voltage change in the sensor for 20 such an equation is between 0.5V to 4V, after amplification of the signal.
2. The hemispherical plunger 16 allows for faithful transmission in various wrist positions.
3. The system does not require any fixation of strap pressure. Its main aim is to pick up the waveform of the pressure in the artery for calibration and calculation of blood pressure values in the software program.

The housing is designed to house the transducer and the plunger and to effect a vertical applanation force against the radial artery when used with an elastic strap. This is achieved by having a smooth convex outer surface (casing cover) with a guard along the side. The smooth convex surface allows the strap to slide over the casing while the guard maintains the strap in place. The casing chamber houses the transducer firmly with the diaphragm surface facing inwards. The inner surface of the housing is designed with seating for the plunger while allowing a pre-determined gap between the plunger surface and the diaphragm. The plunger protrudes from the pre-determined aperture in the inner casing.

The Strap System

Figure 6:
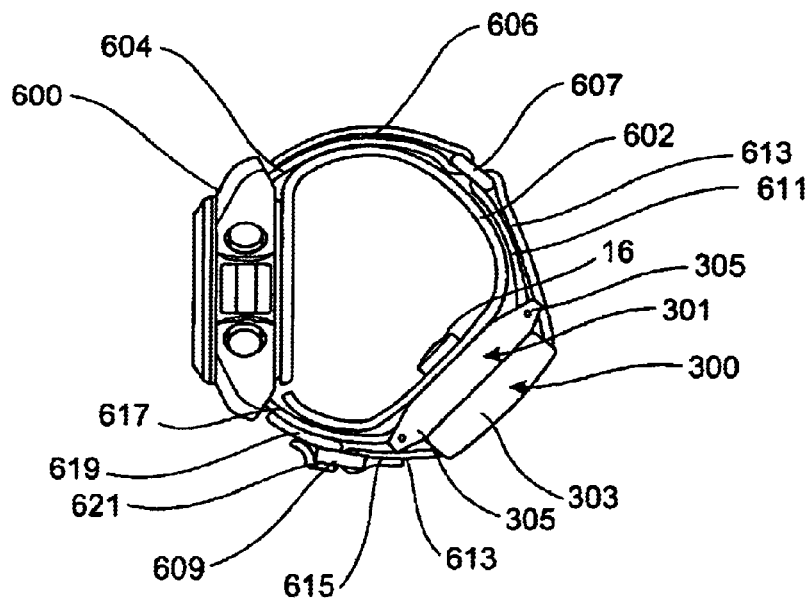
FIG. 6 is a side view of a portable blood pressure monitoring device of the present invention as preferably embodied in a watch.
Figure 7:
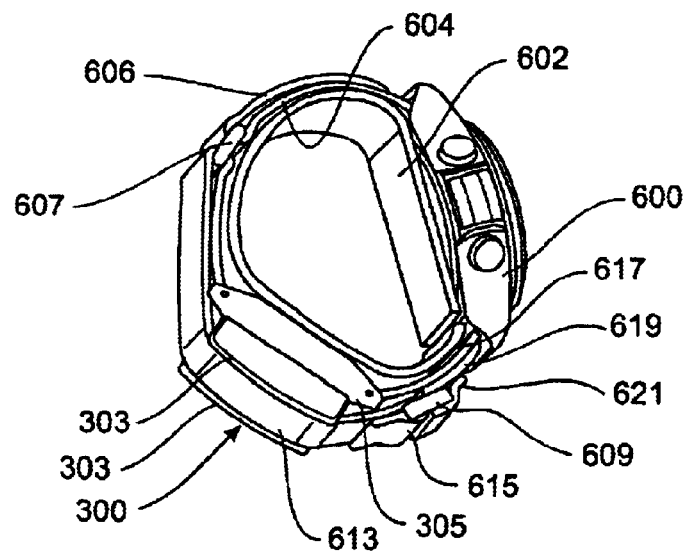
FIG. 7 is a perspective view of the watch of FIG. 6.

Referring to FIGS. 6 and 7, according to the preferred embodiment of the present invention the housing enclosing the sensor is connected with a watch head 600 and with the wrist of a wearer by a system of straps and padding. The watch head 600 includes a first strap 617 extending from one side edge to connect with a first pair of straps securing legs 305 of the carrying portion 301 of the housing. The first strap portion 617 is preferably of a length set for a particular user such that with the watch head 600 against the outer plane of a user's wrist the plunger 16 of the sensor will imponge against the radial aretary. This requires the housing to be skewed to one side of the inner face of the user's wrist. The first strap portion 617 will hereafter be referred to as the radial watch strap 617.

The watch head 600 has a second strap portion 604 extending from its other side edge. The second strap portion 604 will be referred to as the ulnar strap. The ulnar strap 604 has an end 606 that passes outwardly through an oblong ring 607 and back upon itself. This outer end 606 fixes to the inner portion of the ulnar strap 604. This fixing is preferably adjustable, for example by a hook and loop fastener arrangement between the overlap of inner and outer portions. The radial strap 617 and the ulnar strap 604 are preferably substantially non-extensile.

A second oblong securing ring 609 is secured to the radial strap 617. Preferably this securment is by a short connecting loop 619 connected with the radial strap 617 and having an end 621 passing outwardly through the oblong ring 609 to double back on and be secured to itself. An elasticaly extensile strap portion 611 is connected with the second pair of strap connecting legs 305 of the sensor housing. The elastic strap passes outwardly through the oblong ring 607. An outward portion 613 doubles back over the inward portion 611 and passes over the outside of the cover portion 300 of the sensor housing. The strap is constrained to sit over the convex outer surface by side walls 303. The other end 615 of elastic strap 613 passes outwardly through the second oblong ring 609 doubling back and being secured thereto to itself.

A cuff 602 of padding material is provided within the circle of watch head 600, straps 604 and 611, carrying portion 301 of the sensor housing and radial strap 617. The cuff 602 of padding material includes an aperture fitting over plunger 16 of the sensor. An annular double sided self-adhesive pad between the cuff and the sensor housing secures the cuff to the sensor housing with the plunger protruding through the aperture.

With the device in place on a user's wrist and the straps appropriately tensioned the elastic strap 613 extending across the convex surface of the cover portion 300 results in a perpendicular applanation force. It has been found to provide a suitably constant force under a range of user movement.

This consists of 2 segments, namely the sensor segment and the locking segment. The sensor segment has an elastic loop with one end attached to the watch head and the other end to housing, with the elastic portion positioned to slide over the convex surface of the outer casing. This will result in a vertical applanation force on the housing when the elastic loop is pulled.

The convex shape of the housing allows an even spread applied axial force onto the plunger with the aid of the elastic strap portion.

The Electronic Processing Unit

Figure 10:
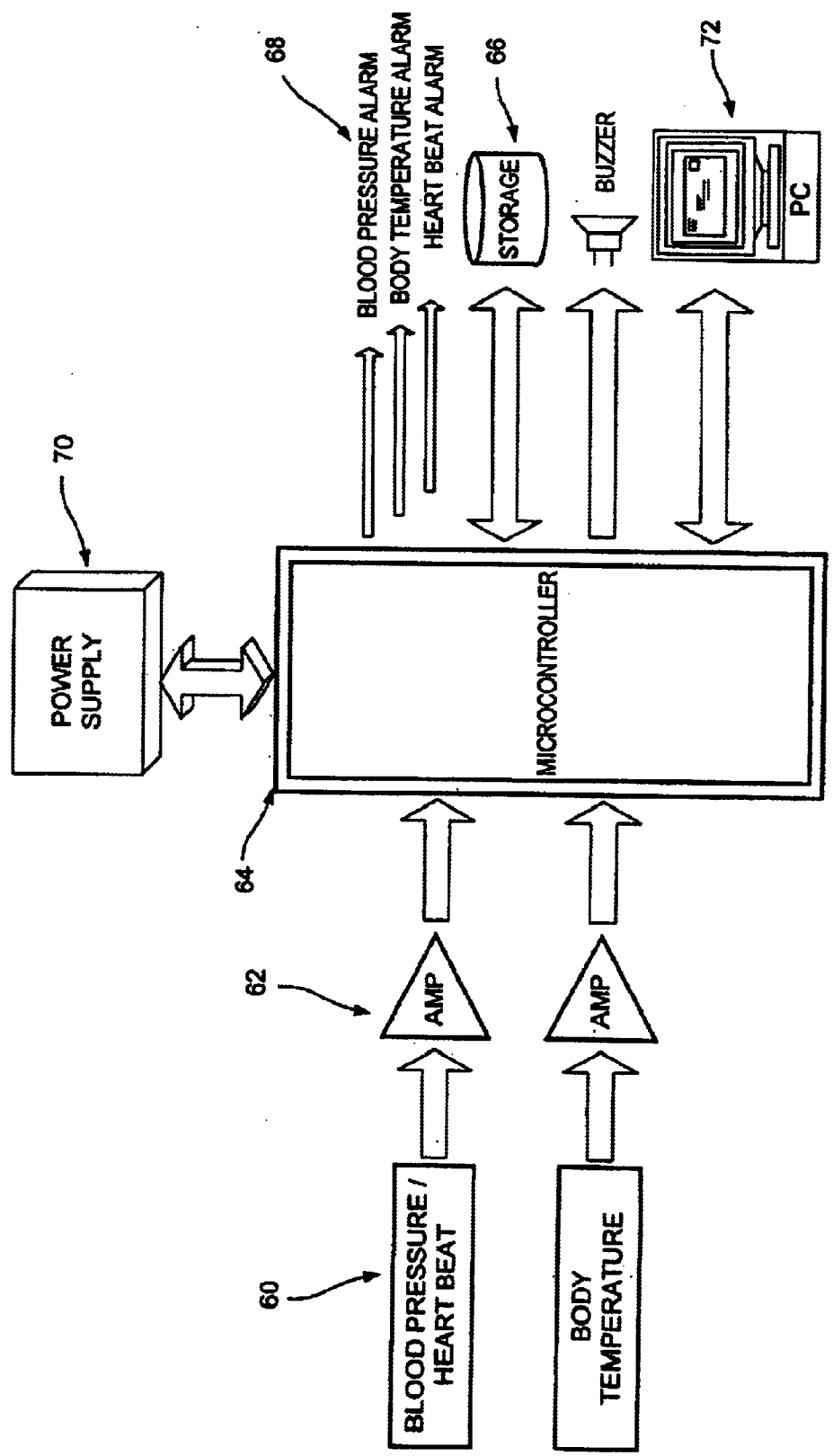
FIG. 10 is a schematic block diagram of a blood pressure monitoring device designed according to the preferred embodiment of the present invention.

FIG. 10 is a schematic block diagram of a blood pressure monitoring device designed according to the preferred embodiment of the present invention. Blood pressure readings 60 are taken by the sensor 10 and are amplified to a value that can be read by a microcontroller/microprocessor 64. An example of the microcontroller/microprocessor 64 suitable for use with the device may be the Motorola 68 series of microprocessor. Optionally, a temperature sensor as found in the art could also be included into the device to read the body temperature, and send the readings to the microcontroller/microprocessor 64. The readings are preferably stored into a storage component 66. The microcontroller/microprocessor 64 may also be coupled to various alarms 68, such as blood pressure, body temperature and heart-beat alarms to warn the user if a pre-determined value is reached. The device is powered by a power supply. The readings, whether taken in real-time or stored in the storage component 66, can be downloaded into a personal computer 72 or other communication device.

In the preferred form of the invention these components, which comprise the electronic processing unit, are housed in the watch 600.

Figure 11:
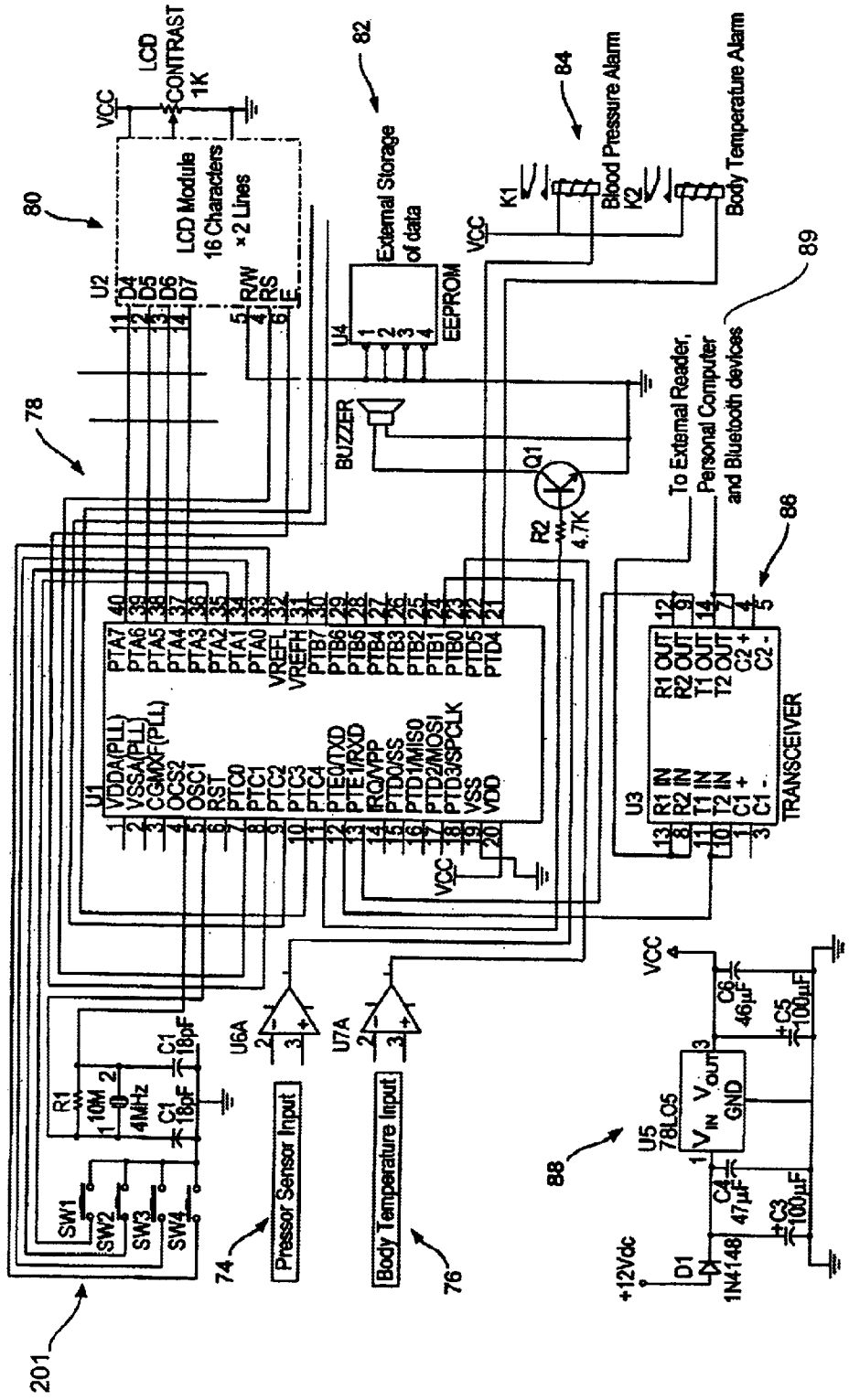
FIG. 11 is a schematic circuit diagram of a blood pressure monitor device designed according to the preferred embodiment shown in FIG. 10.

FIG. 11 is a schematic circuit diagram of a blood pressure monitor device designed according to the preferred embodiment shown in FIG. 10. It demonstrates the circuit connection of the primary components of the device, including the pressure sensor input 74, body temperature input 76, microprocessor 78, liquid-crystal display module 80 for display on the device, the EEPROM storage 82, blood pressure alarm 84, transceiver 86, power supply 88 and button switches 201.

The microprocessor is programmed to perform certain data collection, data processing and data transmission functions. The data collection preferably occurs on a continuous basis. Data processing is preferably performed at least to calculate estimated absolute pressure readings from the electrical sensor readings. This processed data may be then directly uploaded or transmitted for further processing outside the device or may be further processed within the device for either discrete analysis, such as for graphing blood pressures over time, and for waveform analysis as will be described further on.

Data Collection

Figure 12:
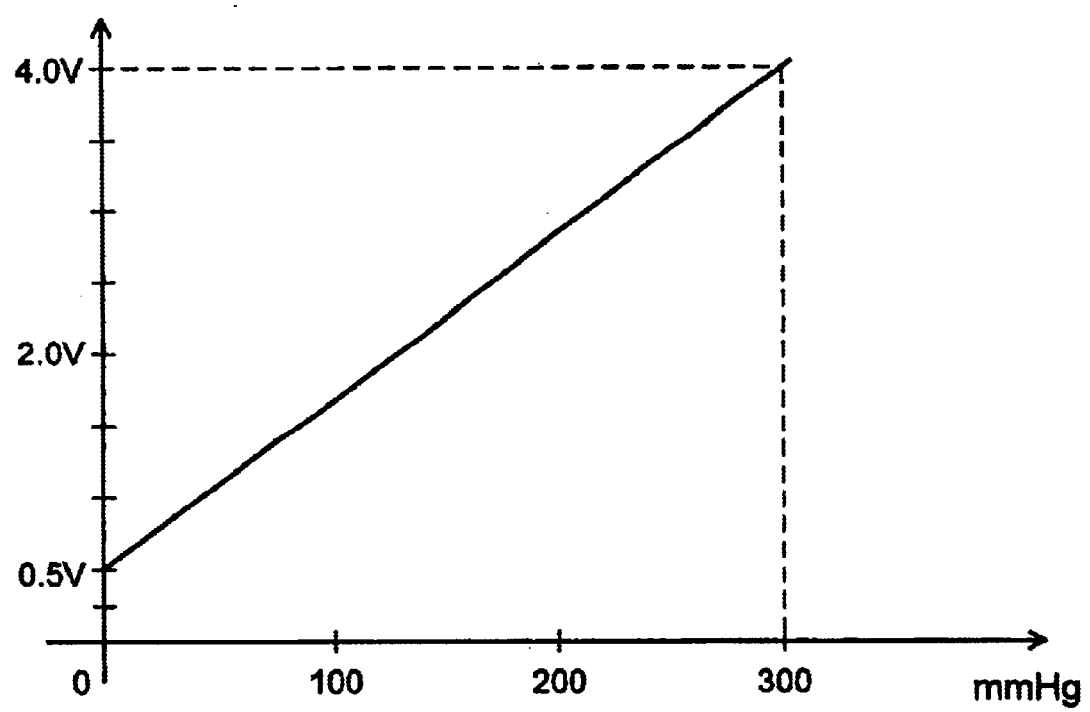
FIG. 12 is a sample graph showing the voltage output produced by the sensor according to the described embodiment in response to a pressure applied to the sensor.

FIG. 12 is a sample graph showing the voltage output produced by the sensor 10 according to the described embodiment in response to a pressure applied to the sensor 10. As mentioned above, the sensor includes a transducer 12. The transducer is preferably one which provides a change in voltage that is directly proportional to the amount of pressure applied onto the transducer to produce a linear graph similar to the one illustrated in FIG. 12. It was found that a suitable transducer is the Foxboro/ICT Model 1865 transducer.

With the sensor system 10 used, and a microprocessor employed in the watch head 28 to calculate the readings produced by the sensor 10, up to 32 values per second were obtained during tests on the device. By varying the intervals of each detection, i.e. the number of values per second, the inventors have been able to obtain optimal waveforms at 32 readings per second. These waveforms correspond to the systolic/diastolic cycle of the heart when the readings were compared simultaneously with conventional Doppler machines.

Figure 13:
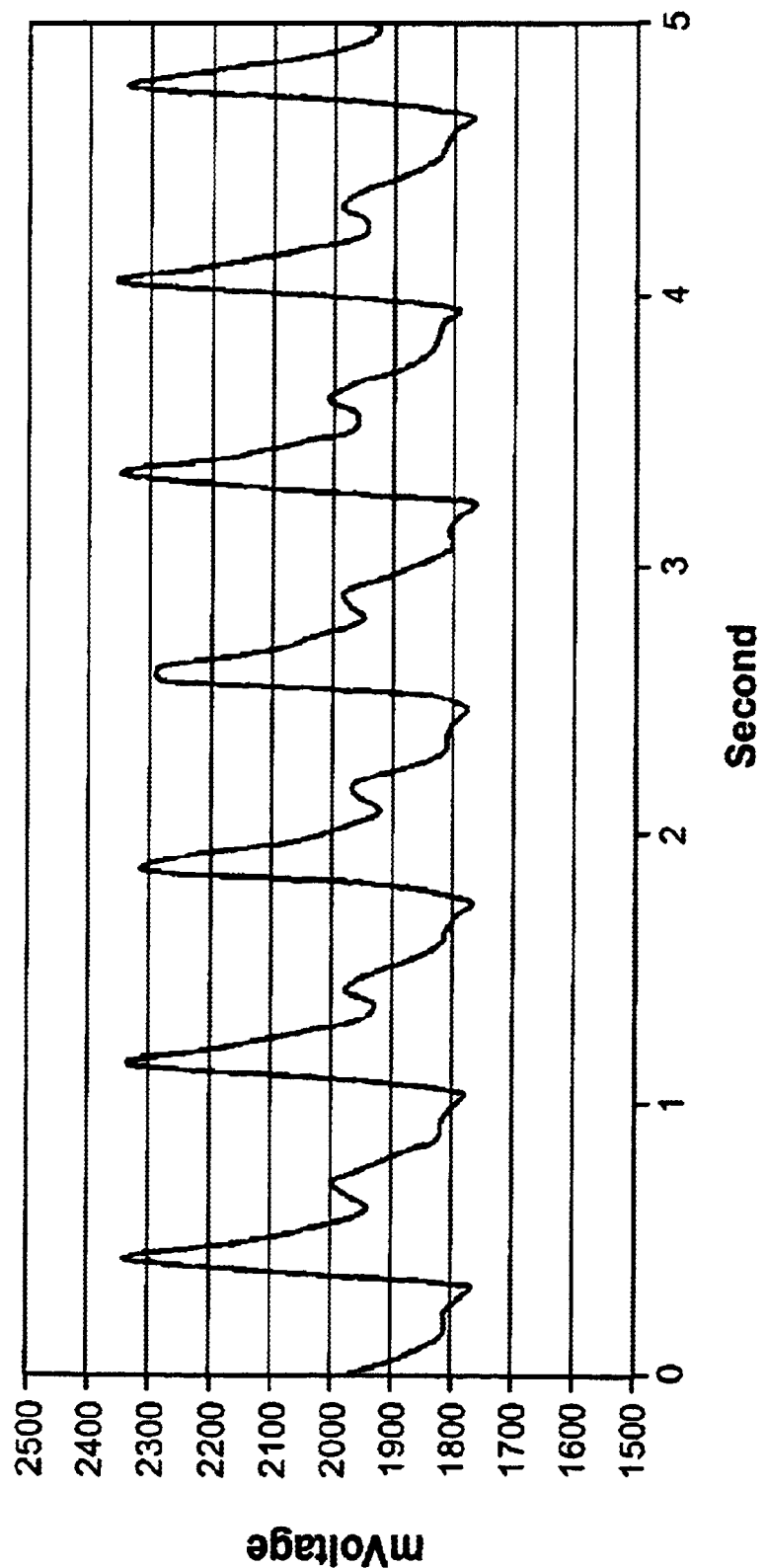
FIG. 13 is a sample chart showing sensor readings of a wearer's blood pressure taken over 6 seconds.

FIG. 13 is a sample chart showing sensor readings of a wearer's blood pressure taken over 6 seconds. There are a total of 6 systolic and 6 diastolic values provided. These systolic and diastolic readings are averaged under the calibration procedure described below.

Figure 8:
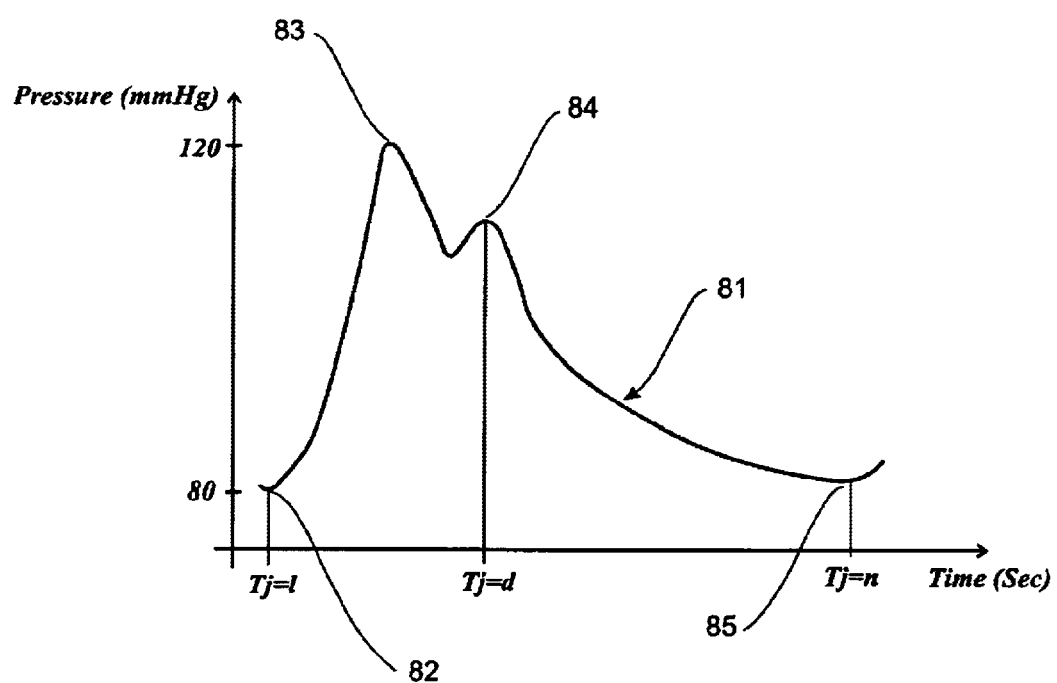
FIG. 8 is a pressure v time graph showing a typical single arterial pulse with its characteristic features.

Referring to FIG. 8 a sample chart is shown being a Pressure v Time graph compiled using the continuous sensor readings rather than discrete readings of FIG. 13. In FIG. 8 the pressure waveform 81 for a single arterial pulse can be seen to begin at a first diastolic trough 82 and end at the next subsequent diastolic trough 85. The waveform 81 includes the systolic peak 83 and the dicrotic notch 84.

Calibration

Figure 14:
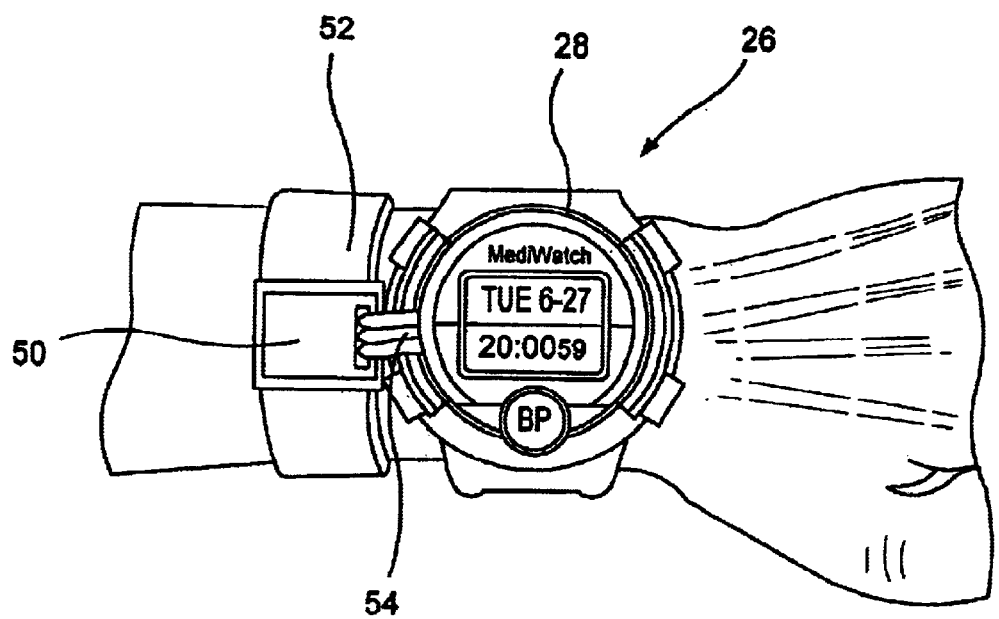
FIG. 14 is a perspective view of an auto-calibrator that is connected to the blood pressure monitoring device for calibration purposes.

FIG. 14 is a perspective view of an auto-calibrator 50 that is connected to the blood pressure monitoring device (watch 26) for calibration purposes.

The auto-calibrator 50 has been designed to give an absolute value of the blood pressure using a conventional occlusive method. The concept is that a separate wrist-band 52 is strapped to the wrist 24 next to the watch 26. The wrist-band 52 uses a cuff system that is automated, self-inflating and measures the absolute blood pressure for reference by the blood pressure monitoring device (watch 26).

Instead of a liquid crystal display on the said auto-calibrator 50, the data read by the wrist-band may be immediately processed by its microprocessor (not shown) and downloaded to the watch 26 via a 3-pin outlet 54 to calibrate the system.

The electronically operated cuff-type non-continuous blood-pressure monitor set at the wrist level is already available in the market. The inventors have designed a software program and a microprocessor to download the systolic and diastolic readings into the watch-head 28 itself.

Simultaneous with the calibrator 50 taking the systolic and diastolic reading, the sensor 10 of the watch 26 takes the blood pressure readings and waveforms of the last 6 seconds. As mentioned, 10 readings are taken per second and 60 readings are therefore taken during the 6 seconds. A sample wave-form has been illustrated in FIG. 13. The average of the peak readings (systolic) are calculated after sampling to obtain greater accuracy. Sampling includes filtering readings that do not correspond to an expected wave-form (for example, muscle contractions produce a sharper and symmetrically-formed peak). Correspondingly, the average of the trough readings (diastolic) are also calculated. The values of the average systolic and diastolic readings respectively are compared to the systolic and diastolic readings from the auto-calibrator 50, to assign absolute values to the sensor readings with reference to a voltage level. It is then verified by the software program using the linear relationship of the pressure against voltage change characterized by the sensor 10 (a chart illustrating the linear relationship is shown in FIG. 12) as a guide.

The calibrator 50 can then be removed and continuous blood pressure monitoring commences. At any one time, the value of the blood pressure can be checked or verified by the calibrator 50 (which reading may be displayed on the watch-head 28). This is useful when the alarm is sounded when, for example, the blood pressure is outside a pre-determined range, or reaches a preset value.

The pulse rate may also be calculated simply by the time interval between 2 systolic or diastolic values divided by 60 seconds. Therefore, this gives a beat-to-beat heart rate and therefore allows verification of the regularity of the heart beat when the data is provided over a period of time.

Steps in Calibration

Figure 15:
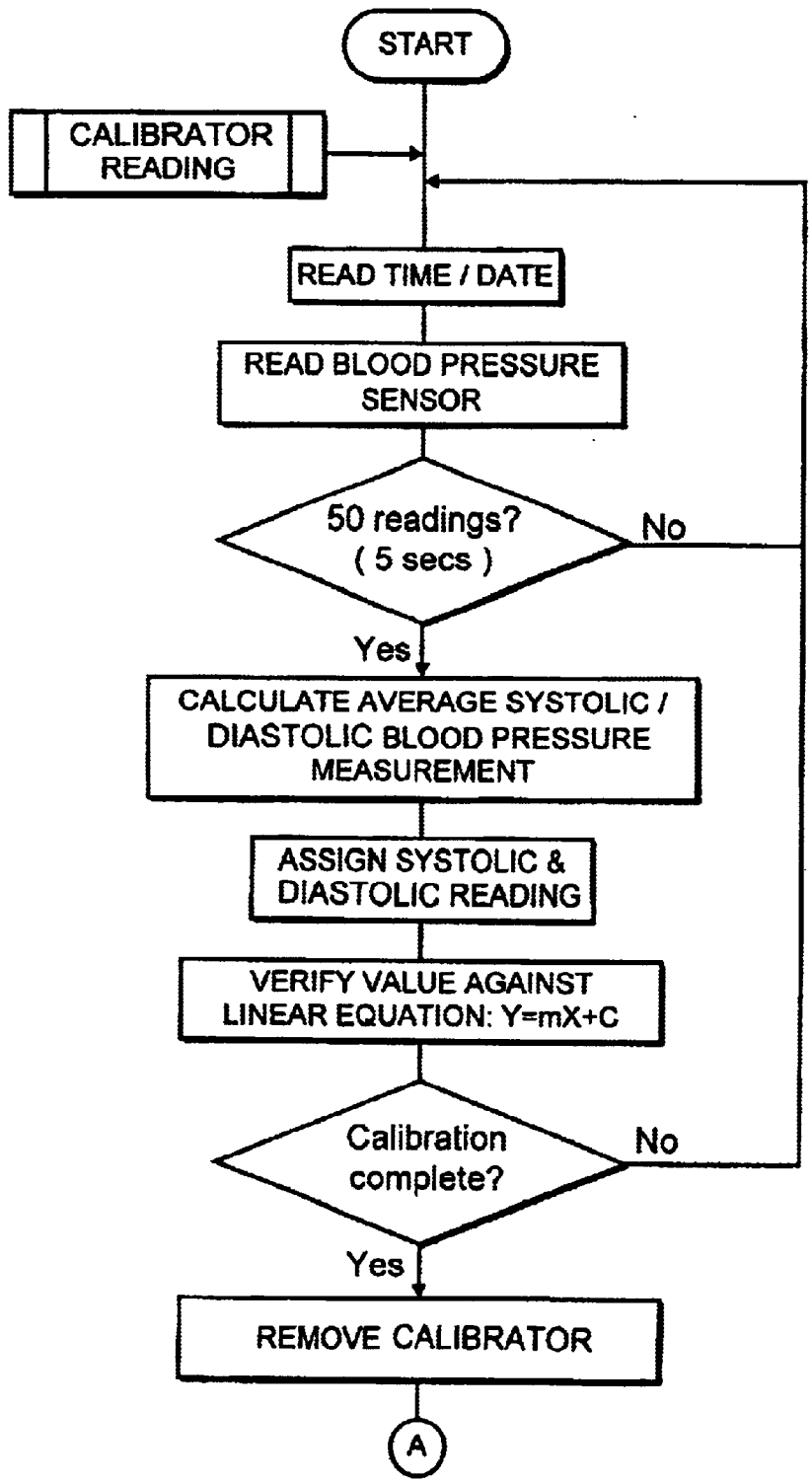
FIG. 15 is a flow-chart summarizing the steps involved in the calibration procedure.

FIG. 15 is a flow-chart summarizing the steps involved in the calibration procedure. In brief, these are to:

1. Put on the auto-calibrator adjacent to the watch in a neutral position of the wrist.

2. Connect the calibrator to the watch through the physical interface.
3. Switch on the calibrator to inflate and deflate the cuff automatically, thereby obtaining the systolic and diastolic readings. These readings are displayed on the watch-head and absolute values are assigned to the sensor readings.
4. Remove the auto-calibrator when calibration is complete.

The processor is programmed to calibrate the arterial pulse waveform from the pressure transducer output using equations 6, 6(a) and 6(b).

In particular the instantaneous blood pressure Pj at a sample point is calculated as:

$$P_j = \left(\frac{P_{sys} - P_{dia}}{A_{max} - A_{min}}\right) \times A_j + C \quad (6)$$

Where: Psys denotes the calibrator measured Systolic Pressure correspond to Amax, Pdia denotes the calibrator measured Diastolic Pressure corresponds to Amin, Amax denotes the maximum measured value of an arterial pulse from the pressure transducer output, Amin denotes the minimum measured value of an arterial pulse from the pressure transducer output, Aj denotes the jth sample measured value of an arterial pulse from pressure transducer output, and C denotes an arbitary constant calculated using one of the equations 6a or 6b.

$$C = P_{sys} - \left(\frac{P_{sys} - P_{dia}}{A_{max} - A_{min}}\right) \times A_{max} \quad (6a)$$

or $$C = P_{dia} - \left(\frac{P_{sys} - P_{dia}}{A_{max} - A_{min}}\right) \times A_{min} \quad (6b)$$

Waveform Processing

A waveform is captured as a series of points from the continuous electrical signal generated by the pressure transducer. A complete arterial waveform including the dicrotic notch is captured. The peaks of the continuous waveform are isolated, the diastolic trough is located and the dicrotic notch is located.

The electrical sensor output is converted to pressure readings using the calibration set forth above with reference to equation 6. The electrical sensor output is also run through a peak gate providing a digital output. The peak gate has a predetermined threshold voltage. When the sensor output is above the threshold voltage the peak gate is "on" or "open". When the sensor voltage is below the threshold voltage the peak gate is "off" or "closed". In the preferred embodiment of the present invention the peak gate threshold is preferably chosen to be approximately in the middle of the pressure transducer range in normal pressure monitoring use. For example if under normal conditions the sensor output ranges between 100 mV and 300 mV then an appropriate peak gate threshold to choose would be 200 mV. The peak gate output is used in the preferred method of locating the systolic peak, diastolic trough and dicrotic notch. The peak gate logic could also be implemented in software, processing either the raw sensor signal or the calibrated pressure reading.

In the preferred embodiment of the invention the systolic peak, diastolic end point and dicrotic notch are located in accordance with the following method:

1. A series of sampling points is captured continuously.
2. Each sampling point is compared with the status of the peak gate, either "Peak gate Open" (PGO) or "Peakgate Close" (PGC).
3. The highest sampling point taken during the "PGO" phase is assigned as the peak Systolic value.
4. From this point, the sampled values will show a downward trend even as the peak gate remains open until the peak gate threshold is reached. After this point, the PGC phase will follow.
5. After the PGC phase resumes the first peak (a rise followed by a fall), is detected. This peak is recorded as the "Dicrotic Notch".
6. The process of detecting the diastolic end point begins when the next PGO is triggered at the peak gate threshold voltage.
7. The sampled values are checked in the reverse direction i.e. comparing each point to the previous one, until the first rise is located. This indicates the diastolic end point. The sample pressure at this time point constitutes the end-diastolic pressure.
8. The logic cycle is repeated for each arterial waveform in turn.

The recorded arterial waveform, and location of the dicrotic notch and diastolic end point are used to calculate certain characteristics. These characteristics include the mean arterial pressure, a mean systolic pressure and a mean diastolic pressure. These calculated characteristics are further used to calculate a mean systolic pressure index and a mean diastolic pressure index.

In particular the microprocessor is programmed to perform calculations in accordance with the following equations.

The Mean Arterial Pressure (MAP) is computed using equation (1), as the area under the pressure waveform between 2 consecutive troughs.

$$MAP(mmHg) = \frac{\sum_{j=1}^{n-1}(P_j + P_{j+1})}{2(n-1)} \quad (1)$$

Where n denotes the total number of samples
Pj denotes the Pressure at sample j
j denotes the index for sample j The Mean Systolic Pressure (MSP) is computed using equation (2), as the area under the curve of a single waveform from the starting point (previous trough) to the dicrotic notch of the waveform.

$$MSP(mmHg) = \frac{\sum_{j=1}^{j=d-1}(P_j + P_{j+1})}{2(d-1)} \quad (2)$$

Where d denotes the sample at the Dicrotic Notch
Pj denotes the Pressure at sample j
j denotes the index for sample j This represents the average pressure during the systolic phase. The MSP index is the index obtained by dividing MSP by MAP as in equation (3):

$$\text{MSP\_Index} = \frac{MSP}{MAP} \quad (3)$$

The Mean Diastolic Pressure (MDP) is computed using equation (4) as the area under the curve starting from the dicrotic notch to the immediate trough. This corresponds to the average pressure during diastole.

$$MDP(mmHg) = \frac{\sum_{j=d}^{j=n-1}(P_j + P_{j+1})}{2(n-d)} \quad (4)$$

Where n denotes the total number of samples
d denotes the sample at the Dicrotic Notch
$P_j$ denotes the Pressure at sample j
j denotes the index for sample j
The MDP index is calculated using equation (5):

$$MDP\_Index = \frac{MDP}{MAP} \quad (5)$$

The mean systolic pressure the mean diastolic pressure the MSP index and the MDP index are believed to be useful quantified measures of the shape of the pressure waveform which will have clinical uses as indicators of one or more medical conditions.

It will be appreciated that final processing of waveforms to produce the MAP, MSP, MDP, MSP_index and MDP_index may be conducted either within the device or externally of the device, for example using waveform data downloaded from the device at intervals or continuously transmitted from the device to a receiving computer or other device.

Figure 16:
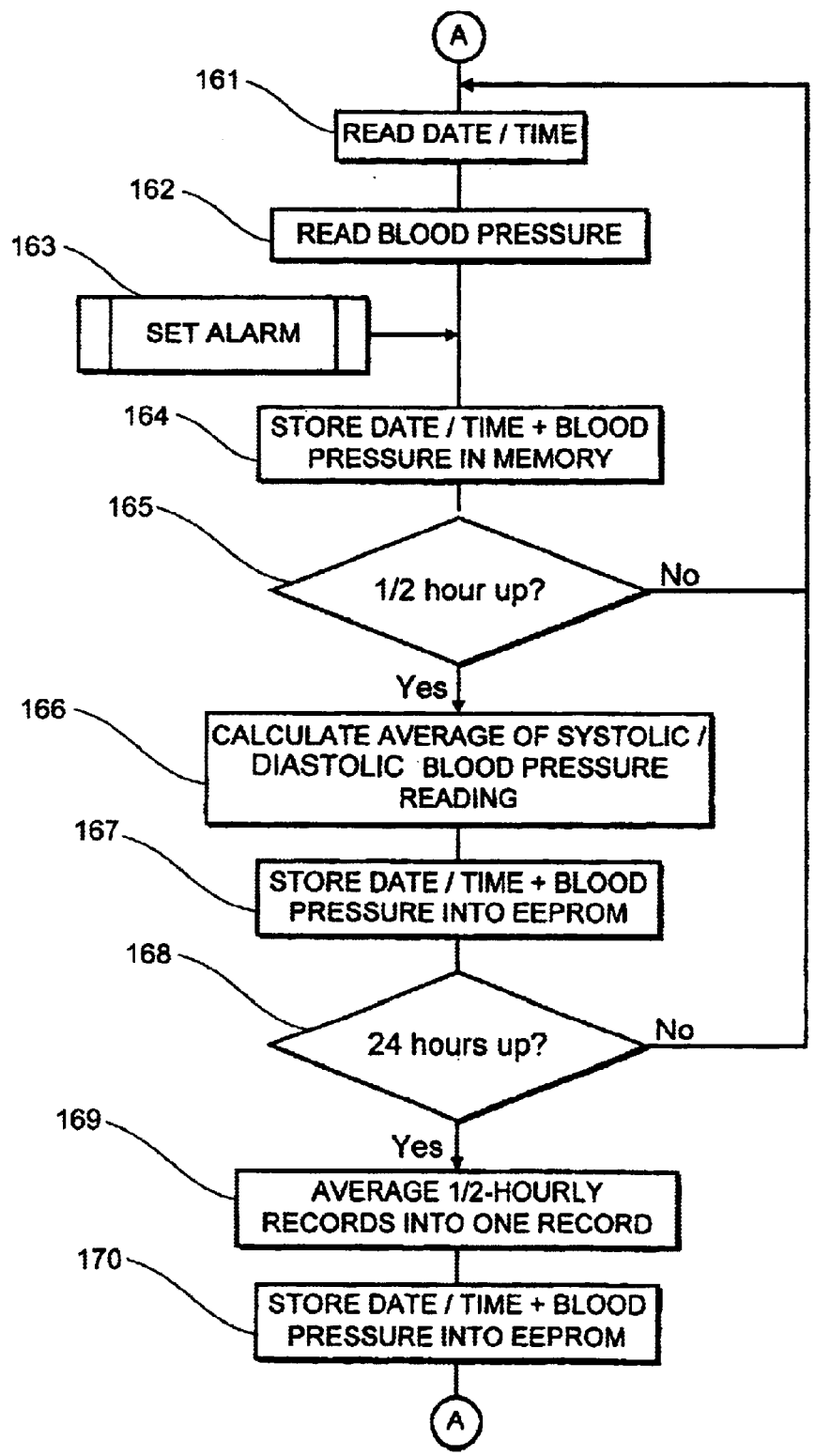
FIG. 16 is a flow-chart summarizing the steps involved in taking blood pressure readings.

Another objective of the collection and storage of data is to be able to see trends in blood pressure readings and determine the danger-point of the change in blood pressure during a pre-determined period of time. Since blood pressure readings are stored in the watch memory module with respect to a time, such trends in change of blood pressure over a period of time can be monitored. FIG. 16 is a flow-chart summarizing the steps involved in taking blood pressure readings.

The sequence of steps involved in taking discrete, pulse by pulse, blood pressure readings begins by executing a blood pressure reading loop of steps 161, 162 and 164. This loop includes reading the date and time from the internal clock of the device at step 161, taking an instantaneous blood pressure reading at step 162 and storing the date and time and associated blood pressure reading in memory at step 164. This loop is executed at short intervals over a one half hour period. Until it has been determined at step 165 that the half hour period has elapsed the loop returns to step 161.

The microprocessor is programmed so that once it determines at step 165 that the half hour is up it proceeds to average and store the blood pressure readings for the just elapsed half hour interval. The microprocessor is programmed to calculate at step 166 average systolic and diastolic blood pressure readings from the readings stored in memory. It is programmed to store at step 167 the current date and time and the average blood pressure readings calculated at step 166 in memory.

The microprocessor is programmed to determine at step 168 whether a full 24 hour time period has elapsed. If not then it returns to step 161 and the pressure reading loop. If the microprocessor determines at step 168 that a 24 hour time period has elapsed it is programmed to proceed to steps 169 and 170.

At step 169 the microprocessor reads the half hourly records for the immediately preceding 24 hour interval and averages these to a single record. At step 170 the microprocessor stores the present date and time and the averaged 24 hour reading into memory. It will be appreciated that in most operating circumstances the device will be repeating the loop of steps 161, 162 and 164. This loop may also include provision for setting or resetting a blood pressure alarm using buttons 201 (e.g.: step 163).

Communication Tool

Figure 17:
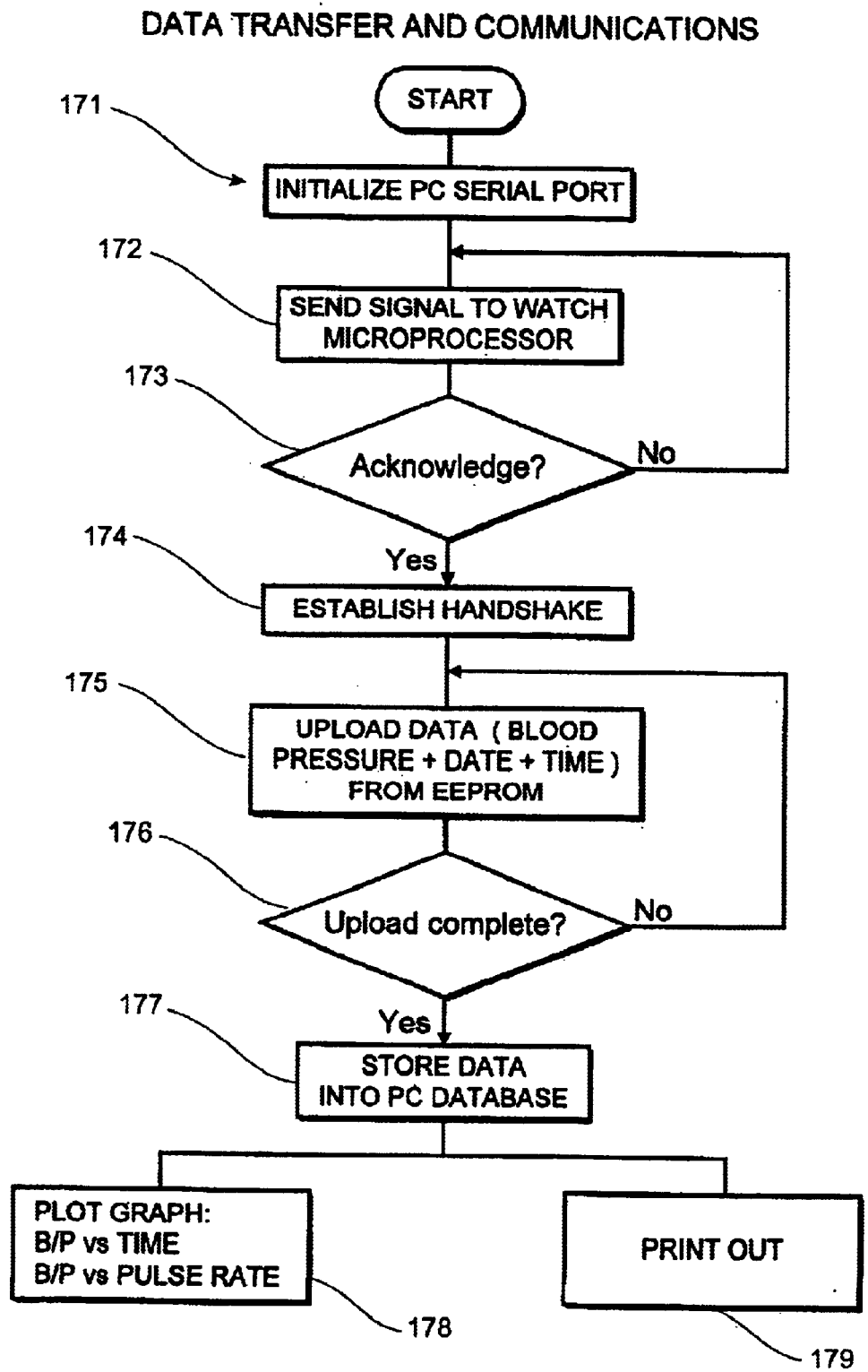
FIG. 17 is a flow-chart summarizing the steps involved in the data transfer and communications aspect of the invention.

The watch is preferably provided with an interface 89 to connect to a personal computer to download data or to a printer to print data. FIG. 17 is a flow-chart summarizing the steps involved in the data transfer and communications aspect of the invention.

The flow chart of FIG. 17 summarises the process that the personal computer software is programmed to implement according to the preferred embodiment of the present invention. In particular the software is programmed to begin by initialising the personal computer serial port at step 171. With the personal computer serial port initialised at step 171 the software proceeds to send a signal to the watch microprocessor at step 172. At step 173 the software determines whether the watch microprocessor has acknowledged the initial communication signal of step 172. If the signal has not been acknowledged it repeats step 172 and continues to loop step 172 until receipt is acknowledged. Once acknowledgement has been received from the watch microprocessor the software proceeds to step 174 and establish full communication through a handshaking process. The software then proceeds to perform a loop of steps 175 and 176 to upload data. At each repetition of step 175 the software uploads a single dataset from the memory of the device. Each reading includes the systolic and diastolic blood pressure readings, date and time. At step 176 the software determines whether the upload is complete. If not it returns and repeats step 175 for the next data set.

Once the microprocessor determines at step 176 that upload is complete the software proceeds to store the uploaded data in a database at step 177. The software provides the capability of printing out the data results, (e.g.: at step 179) and plotting summary graphs such as blood pressure v time and blood pressure v pulse rate, (e.g.: at step 178).

Although the watch may be connected directly to a personal computer by a direct cable connection such as IRS 323, Universal Serial Bus or other similar interface, the watch may advantageously be provided with wireless communication, particularly for the output of continuous waveforms.

Setting of Alarm

Figure 18:
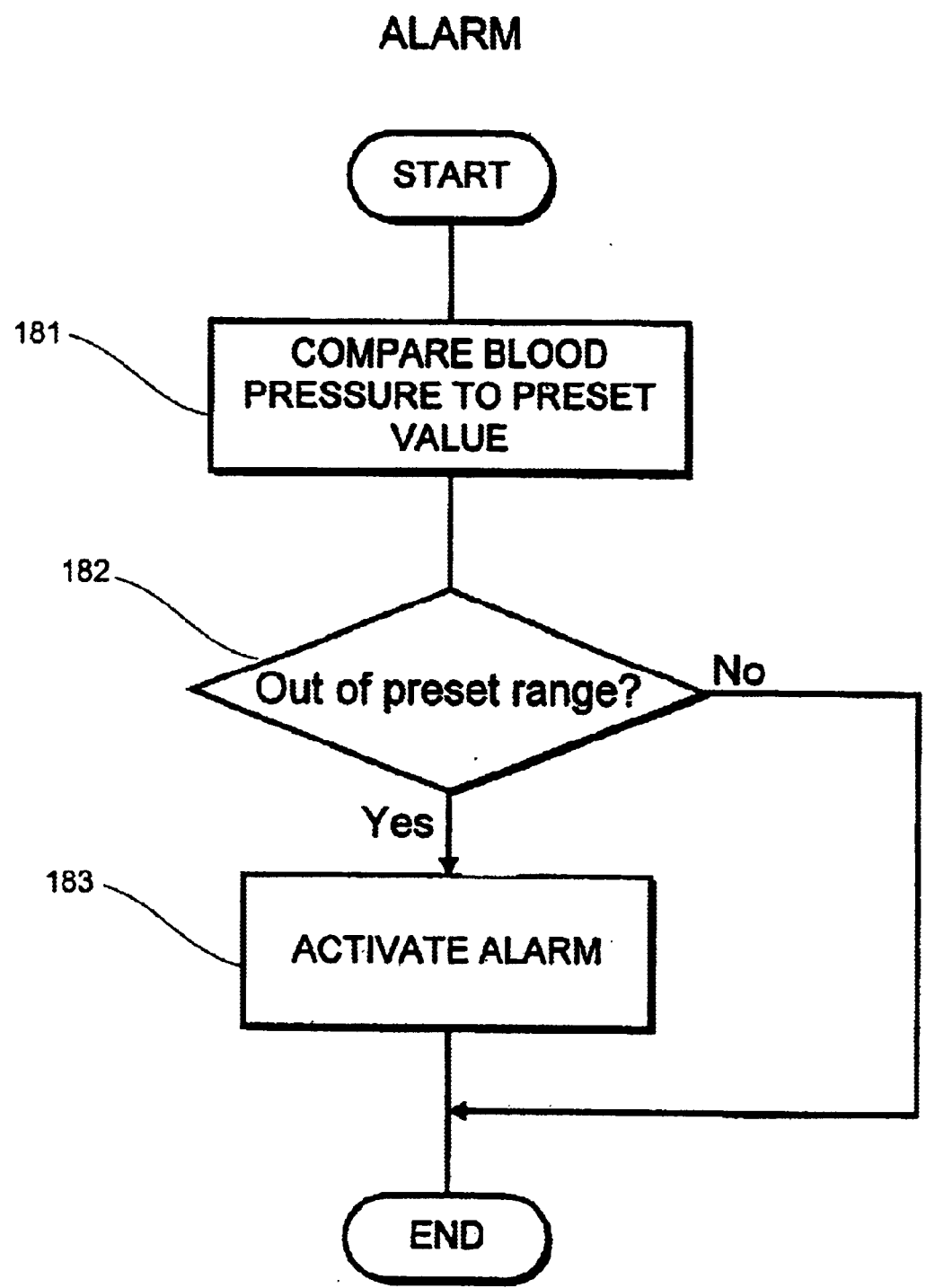
FIG. 18 is a flow-chart summarizing the steps involved in the watch determining whether to sound an alarm to warn of potentially dangerous blood pressure levels.

It is believed that many catastrophic events occur when the blood pressure suddenly increases or decreases drastically in a patient. This is true in some stroke patients and very evident in pre-eclampsia patients. The aim of the continuous monitoring is firstly to discover and help the control of blood pressure. Secondly, in some cases, a tragedy may be avoided if there is an alarm system to detect these sudden and drastic changes. The alarm thresholds can be preset at the factory or individually set using buttons 201, and multiple alarms can be set for the blood pressure or pulse rates. FIG. 18 is a flow-chart summarizing the steps involved in setting the alarm in the watch to warn of potentially dangerous blood pressure levels.

In particular the microprocessor is programmed to perform a continuing loop in conjunction with its data collection loop of steps 161, 162 and 164 of FIG. 16. This loop begins with a step 181 of comparing the presently read blood pressure with a value as presently set using the set alarm function of step 163 in FIG. 16.

The microprocessor proceeds to determine whether the blood pressure value is outside the set range at step 182. If the blood pressure is outside the set range at step 182 then it proceeds to end the loop, which will be repeated each time a blood pressure reading is taken. If the microprocessor determines at step 182 that the blood pressure is outside the set range then it proceeds to step 183 to activate an alarm.

While a particular embodiment of the invention has been shown and described, it will be obvious to those skilled in the art that changes and modifications of the present invention may be made without departing from the invention in its broader aspects. As such, the scope of the invention should not be limited by the particular embodiment and specific construction described herein but should be defined by the appended claims and equivalents thereof. Accordingly, the aim in the appended claims is to cover all such changes and modifications as fall within the spirit and scope of the invention.

What is claimed is:

1. A device for non-invasive continuous monitoring of a user's arterial blood pressure that is capable of being used as an ambulatory beat-to-beat blood pressure monitor (ABMP) including,
    sensing means adapted to continuously detect said blood pressure and to generate signals representative thereof by contact with an external surface of the user's body at a location adjacent an artery;
    microprocessing means for interpreting said signals generated by the sensing means to determine actual arterial blood pressure;
    wherein the microprocessing means is programmed to:
        record a complete and continuous arterial pulse waveform,
        detect at least the dicrotic notch and the diastolic trough within a continuous arterial pulse waveform,
        calculate a mean diastolic pressure as the mean sensed pressure between said detected dicrotic notch and the immediately following diastolic trough,
        calculate a mean arterial pressure as the average pressure between two consecutive said diastolic troughs, and
        calculate a mean diastolic pressure index as the quotient of the calculated mean diastolic pressure divided by the mean arterial pressure.

2. A device for non-invasive continuous monitoring of a user's arterial blood pressure that is capable of being used as an ambulatory beat-to-beat blood pressure monitor (ABMP) including,
    sensing means adapted to continuously detect said blood pressure and to generate signals representative thereof by contact with an external surface of the user's body at a location adjacent an artery;
    microprocessing means for interpreting said signals generated by the sensing means to determine actual arterial blood pressure;
    wherein the microprocessing means is programmed to:
        record a complete and continuous arterial pulse waveform,
        detect at least the dicrotic notch and the diastolic trough within a continuous arterial pulse waveform, and
        calculate a mean systolic pressure as the average pressure between the diastolic trough and the immediately subsequent dicrotic notch.

3. A device for non-invasive continuous monitoring of a user's arterial blood pressure that is capable of being used as an ambulatory beat-to-beat blood pressure monitor (ABMP) including,
    sensing means adapted to continuously detect said blood pressure and to generate signals representative thereof by contact with an external surface of the user's body at a location adjacent an artery;
    microprocessing means for interpreting said signals generated by the sensing means to determine actual arterial blood pressure;
    wherein the microprocessing means is programmed to:
        record a complete and continuous arterial pulse waveform,
        detect at least the dicrotic notch and the diastolic trough within a continuous arterial pulse waveform,
        calculate a mean diastolic pressure as the mean sensed pressure between said detected dicrotic notch and the immediately following diastolic trough,
        calculate a mean arterial pressure as the average pressure between two consecutive said diastolic troughs, and
        calculate a mean systolic pressure index as the quotient of the calculated mean systolic pressure divided by the mean arterial pressure.

4. A device for non-invasive continuous monitoring of a user's arterial blood pressure that is capable of being used as an ambulatory beat-to-beat blood pressure monitor (ABMP) including,
    sensing means adapted to continuously detect said blood pressure and to generate signals representative thereof by contact with an external surface of the user's body at a location adjacent an artery;
    microprocessing means for interpreting said signals generated by the sensing means to determine actual arterial blood pressure;
    wherein the microprocessing means is programmed to:
        record a complete and continuous arterial pulse waveform;
        detect the peak systolic pressure and record the peak systolic pressure for at least a selection of recorded arterial pulses, and
        detect the diastolic trough and record a pressure at the diastolic trough for each pulse of said at least selection of arterial pulses.

5. A device as claimed in claim 4 wherein said device includes an alarm and said microprocessing means is programmed to operate said alarm in response to an indicator falling outside a preselected range, said indicator being selected from: said systolic peak pressure, said diastolic trough pressure or the difference between said systolic peak pressure.

6. A device as claimed in claim 5 wherein said device includes user input means, and said microprocessing means is programmed to allow setting or selection of a threshold for said indicator.

7. A device as claimed in claim 6 wherein said microprocessing means is programmed to calculate an average systolic pressure as the average of the pressure as recorded at said systolic peak for said at least selection of arterial pulses and an average diastolic pressure as the average pressure recorded at said diastolic trough for said at least selection of arterial pulses.

8. A device for non-invasive continuous monitoring of a user's arterial blood pressure that is capable of being used as an ambulatory beat-to-beat blood pressure monitor (ABMP) including,
    sensing means adapted to continuously detect said blood pressure and to generate signals representative thereof by contact with an external surface of the user's body at a location adjacent an artery;
    microprocessing means for interpreting said signals generated by the sensing means to determine actual arterial blood pressure, wherein the microprocessing means is programmed to record a complete and continuous arterial pulse waveform;

a first housing holding said sensor sensing means;

a second housing enclosing said microprocessing means; and at least one strap connecting said first housing and said second housing and together therewith forming a band to encircle the wrist of a wearer, said first housing having an outwardly facing pressure surface, with at least one said strap passing freely over said pressure surface.

9. A device for non-invasive continuous monitoring of a user's arterial blood pressure that is capable of being used as an ambulatory beat-to-beat blood pressure monitor (ABMP) including, sensing means adapted to continuously detect said blood pressure and to generate signals representative thereof by contact with an external surface of the user's body at a location adjacent an artery;

microprocessing means for interpreting said signals generated by the sensing means to determine actual arterial blood pressure, wherein the microprocessing means is programmed to record a complete and continuous arterial pulse waveform;

a first housing holding said sensing means;

a second housing enclosing said microprocessing means; and at least one strap connecting said first housing and said second housing and together therewith forming a band to encircle the wrist'of a wearer, said first housing having an outwardly facing pressure surface, with at least one said strap being an elastic strap passing freely over said pressure surface;

wherein said at least one strap includes a second strap connecting between said first and second housing and a third strap connected with said second housing and said elastic strap, said elastic strap being connected at one end to said first housing, extending from there to said third strap before turning back upon itself to form a loop, said loop being connected to said third strap, to then pass over said pressing surfaces of said first housing, with the other end of said elastic strap being connected to said second housing or to said second strap.

10. A device as claimed in claim 9 including a joining ring, said elastic strap passing through said joining ring at said loop, and said third strap passing through said joining ring and back upon itself to have inner and outer portions and to hold said joining ring within a loop thereof, said third strap including adjustable connection means operating between said inner and outer portions.

11. A device for non-invasive continuous monitoring of a user's arterial blood pressure that is capable of being used as an ambulatory beat-to-beat blood pressure monitor (ABMP) including, sensing means adapted to continuously detect said blood pressure and to generate signals representative thereof by contact with an external surface of the user's body at a location adjacent an artery;

microprocessing means for interpreting said signals generated by the sensing means to determine actual arterial blood pressure wherein the microprocessing means is programmed to record a complete and continuous arterial pulse waveform;

a first housing holding said sensing means;

a second housing enclosing said microprocessing means;

at least one strap connecting said first housing and said second housing and together therewith forming a band to encircle the wrist of a wearer, said first housing having an outwardly facing pressure surface, with at least one said strap passing freely over said pressure surface; and a padding cuff disposed within said band, said padding cuff including an aperature, said sensor including a plunger protruding from said first housing through said aperture, and said cuff being adhered to an inner face of said first housing.

12. A method for continuous monitoring of a user's arterial blood pressure including the steps of:

recording a complete and continuous arterial pulse pressure waveform, locating at least the dicrotic notch and the diastolic trough within said continuous arterial pulse waveform, and calculating at least one parameter using said waveform and said diastolic trough and dicrotic notch locations including calculating a mean diastolic pressure as the mean recorded pressure between a said detected dicrotic notch and the immediately following diastolic trough and including calculating a mean arterial pressure as the average pressure between two consecutive said diastolic troughs, and calculating a mean diastolic pressure index as the quotient of the calculated mean diastolic pressure divided by the mean arterial pressure.

13. A method as claimed in claim 12 including calculating a mean systolic pressure as the average pressure between a diastolic trough and the immediately subsequent dicrotic notch.

14. A method as claimed in claim 13 including calculating a mean arterial pressure as the average pressure between two consecutive diastolic troughs, and calculating a mean systolic pressure index as the quotient of the calculated mean systolic pressure divided by the mean arterial pressure.

* * * * *

UNITED STATES PATENT AND TRADEMARK OFFICE
CERTIFICATE OF CORRECTION

PATENT NO. : 6,918,879 B2
DATED : July 19, 2005
INVENTOR(S) : Choon Meng Ting et al.

It is certified that error appears in the above-identified patent and that said Letters Patent is hereby corrected as shown below:

Title page,
Insert Item:
-- [30] Foreign Application Priority Data
Oct. 9, 2000    (SG)    200005776-0 --.

Signed and Sealed this

Eighth Day of November, 2005

JON W. DUDAS
*Director of the United States Patent and Trademark Office*